(12) United States Patent
Chu et al.

(10) Patent No.: US 8,242,120 B2
(45) Date of Patent: Aug. 14, 2012

(54) CARBOCYCLIC COMPOUNDS AND METHODS FOR TREATING EMERGING DISEASE, INCLUDING INFLUENZA AND VENEZUELA EQUINE ENCEPHALITIS VIRUS

(75) Inventors: David Chu, Statham, GA (US); Jagadeeshwar Rao, Mohali (IN)

(73) Assignee: University of Georgia Research Foundation, Inc., Athens, GA (US)

( * ) Notice: Subject to any disclaimer, the term of this patent is extended or adjusted under 35 U.S.C. 154(b) by 195 days.

(21) Appl. No.: 12/450,531

(22) PCT Filed: Apr. 9, 2008

(86) PCT No.: PCT/US2008/004568
§ 371 (c)(1),
(2), (4) Date: Feb. 3, 2010

(87) PCT Pub. No.: WO2008/124157
PCT Pub. Date: Oct. 16, 2008

(65) Prior Publication Data
US 2010/0144664 A1    Jun. 10, 2010

Related U.S. Application Data

(60) Provisional application No. 60/922,701, filed on Apr. 10, 2007.

(51) Int. Cl.
| | |
|---|---|
| *A01N 43/04* | (2006.01) |
| *C07D 239/42* | (2006.01) |
| *C07D 401/04* | (2006.01) |
| *C07D 471/04* | (2006.01) |
| *C07D 471/22* | (2006.01) |
| *C07D 487/04* | (2006.01) |

(52) U.S. Cl. ........................................ 514/256; 514/257
(58) Field of Classification Search .................... None
See application file for complete search history.

(56) References Cited

U.S. PATENT DOCUMENTS

2003/0087873 A1    5/2003    Stuyver et al.

OTHER PUBLICATIONS

Schoneboom, B.A., K.M. Catlin, A.M. Marty, and F.B. Grieder. 2000. Inflammation is a component of neurodegeneration in response to Venezuelan equine encephalitis virus infection in mice. J Neuroimmunol. 109: 132-46.

Charles, P.C., J. Trgovcich, N.L. Davis, and R.E. Johnston. 2001. Immunopathogenesis and immune modulation of Venezuelan equine encephalitis virus-induced disease in the mouse. Virology. 284: 190-202.

De Clercq, E., J. Murase, and V.E. Marquez. 1991. Broad-spectrum antiviral and cytocidal activity of cyclopentenylcytosine, a carbocyclic nucleoside targeted at CTP synthetase. Biochem Pharmacol. 41: 1821-9.

Neyts, J., A. Meerbach, P. McKenna, and E. De Clercq. 1996. Use of the yellow fever virus vaccine strain 17D for the study of strategies for the treatment of yellow fever virus infections. Antiviral Res. 30: 125-32.

De Clercq, E., R. Bernaerts, Y.F. Shealy, and J.A. Montgomery. 1990. Broad-spectrum antiviral activity of carbodine, the carbocyclic analogue of cytidine. Biochem Pharmacol. 39: 319-25.

*Primary Examiner* — Traviss C McIntosh, III
(74) *Attorney, Agent, or Firm* — Henry D. Coleman; R. Neil Sudol; William J. Sapone (57) ABSTRACT

The present invention relates to the use of carbodine and 5-F carbodine and analogs thereof for use in the treatment or prophylaxis of influenza, in particular the H5N1 strain of Avian Influenza A virus or "bird flu" strain of influenza as well as the treatment or prophylaxis of Venezuela equine encephalitis virus or VEE.

3 Claims, 4 Drawing Sheets

FIGURE 1

Table 1 COMPARISON OF the Activity of CARBODINE ENANTIOMERS

| VIRUS | VIRUS DILUTION | DRUG | VISUAL EC50 | VISUAL IC50 | VISUAL SI | N. RED EC50 | NEUTRAL RED IC50 | N. RED SI | VYR-EC90 |
|---|---|---|---|---|---|---|---|---|---|
| DUCK | 1/1000 | Neg. Enantiomer Carbodine | 0.57 | >100 | 175 | 0.87 | >100 | >115 | 0.22 |
| DUCK | 1/1000 | Pos. Enantiomer ribivirin | >100 | >100 | >1 | >100 | >100 | >1 | >100 |
| DUCK | 1/1000 | Racemic Carbodine | 2.7 | >100 | >37 | 5.3 | >100 | >19 | 11.4 |
| DUCK | 1/1000 | ribivirin | 5.7 | >320 | >56 | 5.8 | >320 | >55 | 6.5 |
| GULL | 1/100 | Neg. Enantiomer Carbodine | 0.27 | >100 | 370 | 0.31 | >100 | 323 | 0.22 |
| GULL | 1/100 | Pos. Enantiomer ribivirin | >100 | >100 | >1 | >100 | >100 | >1 | >100 |
| GULL | 1/100 | Racemic Carbodine | 1.8 | >100 | >56 | 1.9 | >100 | >53 | 1.3 |
| GULL | 1/100 | ribivirin | 5.7 | >320 | >56 | 5.9 | >320 | >54 | 3.7 |
| HK/2003 | 1/100 | Neg. Enantiomer Carbodine | 0.18 | >100 | 556 | 0.3 | > | 333 | 0.35 |
| HK/2003 | 1/100 | Pos. Enantiomer ribivirin | >100 | >100 | >1 | >100 | >100 | >1 | >100 |
| HK/2003 | 1/100 | Racemic Carbodine | 0.7 | >100 | >143 | 1.7 | >100 | >59 | 4.6 |
| HK/2003 | 1/100 | ribivirin | 0.57 | >320 | >561 | 1.4 | >320 | >229 | 3.5 |
| VN | 1/500 | Neg. Enantiomer Carbodine | 0.18 | >100 | >556 | 0.19 | >100 | 526 | 0.11 |
| VN | 1/500 | Pos. Enantiomer ribivirin | >100 | >100 | >1 | >100 | >100 | >1 | >100 |
| VN | 1/500 | Racemic Carbodine | 0.57 | >100 | >175 | 0.92 | >100 | >109 | 1.9 |
| VN | 1/500 | ribivirin | 0.39 | >320 | >821 | 0.59 | >320 | >542 | 0.44 |

FIGURE 2

Table 2 Effects of 5-F-carbodine on avian influenza A H5N1 viruses or hybrid viruses.

| H5N1 Influenza A Strain | Visual Assay | | | Neutral Red Uptake Assay | | | Virus Yield Reduction Assay |
|---|---|---|---|---|---|---|---|
| | EC50 (µg/ml) | IC50 (µg/ml) | SI | EC50 (µg/ml) | IC50 (µg/ml) | SI | EC90 (µg/ml) |
| Duck MN/1525/81 Trial 1 | 2.4 | >100 | >42 | 2 | >100 | >50 | ND |
| Duck MN/1525/81 Trial 2 | 1.1 | >100 | >91 | 2.4 | >100 | >42 | 24 |
| Vietnam/1203/04 X H1N1 Ann Arbor/6/60 | 0.81 | >100 | >120 | 0.86 | >100 | >120 | ND |

Figure 3

Table 3. *In vitro* antiviral activity of (-)-Carbodine[20]

| Structure | Viruses | EC$_{50}$ (μM) | IC$_{50}$ (μM) |
|---|---|---|---|
|  | VenezuelanEquine Encephalitis | 0.2 | >100 |
| | Yellow Fever | 1.8 | >100 |
| | Flu A (DUCK)-H5N1 | 0.87 | >100 |

FIGURE 4

Table 4. Expt. NIA-702. Effect of Post-virus Exposure i.p. carbodine Treatment on Survival and Weight Change of C3H/HeN Mice Infected with Venezuelan Equine Encephalitis Virus

*Animals*: Female 16-18 g C3H/HeN mice.

*Virus*: VEE (TC-83 strain), $10^{6.4}$ $CCID_{50}$

*Virus route*: intranasal

*Duration of experiment*: 21 days

*Drug diluent*: 10% DMSO in saline

| Treatment | Dosage | Treatment schedule | Toxicity controls | | Infected, treated | | |
|---|---|---|---|---|---|---|---|
| | | | Alive/ total | Mean wt. change$^a$ (g) | Alive/ total | Mean wt. change$^a$ (g) | $MDD^b$ ± SD |
| Carbodine | 200 mg/kg/d | bid X 8 d beg. 2 dpi | 3/3 | 1.1 ± 0.2 | 9/10*** | -1.0 ± 0.7*** | 12.0 ± 0.0*** |
| Carbodine | 200 mg/kg/d | bid X 8 d beg. 4 dpi | -- | -- | 9/10*** | -0.3 ± 0.9*** | 11.0 ± 0.0*** |
| Ampligen | 12 mg | -4 h and 2 dpi | -- | -- | 4/10*** | 0.1 ± 1.5*** | 12.3 ± 2.9*** |
| 10% DMSO | -- | bid X 8 d beg. -4 h | -- | -- | 0/10 | -2.8 ± 1.0 | 9.1 ± 0.6 |
| Normal Controls | -- | -- | 5/5 | 0.9 ± 0.3 | -- | -- | -- |

CARBOCYCLIC COMPOUNDS AND METHODS FOR TREATING EMERGING DISEASE, INCLUDING INFLUENZA AND VENEZUELA EQUINE ENCEPHALITIS VIRUS

This application claims the benefit of priority of U.S. provisional application Ser. No. US60/922,701, filed Apr. 10, 2007, which is incorporated by reference in its entirety herein.

CLAIM OF PRIORITY AND GOVERNMENT RIGHTS

The work which gave rise to this patent application was supported by a government grant, NIH (1 UO19 AI056540). Consequently, the government retains certain rights in the invention.

FIELD OF THE INVENTION

The present invention relates to the use of carbodine and 5-F carbodine and analogs thereof for use in the treatment or prophylaxis of influenza, in particular the H5N1 strain of Avian Influenza A virus or "bird flu" strain of influenza as well as the treatment or prophylaxis of Venezuela equine encephalitis virus or VEE.

BACKGROUND OF THE INVENTION

In 1997, highly pathogenic avian influenza H5N1 was transmitted from poultry to humans in Hong Kong, resulting in eighteen infected people and six deaths, and reemerged in 2003 causing two similar cases with one fatality. In 2003-2005, extensive outbreaks of H5N1 influenza occurred in nine Asian countries resulting in 19 human cases in Thailand, 91 in Vietnam, seven in Indonesia, and four in Cambodia, with a total of 62 reported deaths. Furthermore, H5N1 infections in family clusters have raised the possibility of human-to-human transmission. As human exposure to and infection with H5N1 viruses continues to increase, so, too, does the likelihood of the generation of an avian-human reassortment virus that may be transmitted efficiently within the global human population, which currently lacks H5N1 specific immunity. Such reassortment events between avian-human and swine-human influenza A viruses have been associated with the 1957 and 1968 influenza pandemics; the 1918 pandemic events remain unclear.

Concern over the potential for the generation of a pandemic H5 strain and its concomitant morbidity and mortality are spurring the search for effective agents against same.

BRIEF DESCRIPTION OF THE INVENTION

The present invention relates to carbocyclic nucleoside compounds according to the structure:

Wherein R is H or F;
$R^1$ and $R^{1a}$ are each independently H, an acyl group, a $C_1$-$C_{20}$ alkyl or ether group, an amino acid residue (D or L), a phosphate, diphosphate, triphosphate or phosphodiester group or together $R^1$ and $R^{1a}$ form a carbodiester or phosphodiester group with the oxygen atoms to which they are bonded;

$R^2$ is H, an acyl group, a $C_1$-$C_{20}$ alkyl or ether group or an amino acid residue;

And pharmaceutically acceptable salts, enantiomers, hydrates and solvates thererof.

Preferably $R^{1a}$ is H. Also preferably, $R^1$ and $R^2$ are both H.

The present invention also relates to pharmaceutical compositions comprising an effective amount of a compound as described above, optionally in combination with a pharmaceutically acceptable carrier, additive or excipient.

Methods of treatment represent further embodiments according to the present invention. In this aspect a method of treating or reducing the likelihood of a an Avian influenza A H5N1 strain viral infection or a Venezuelan equine encephalitis viral infection comprising administering to a patient in need of therapy or at risk for infection thereof an effective amount of a compound as otherwise described above.

BRIEF DESCRIPTION OF THE FIGURES

FIG. 1 shows a comparison of the activity of carbodine enantiomers against four strains of H5N1 influenza (bird flu).

DETAILED DESCRIPTION OF THE INVENTION

The following definitions are used to describe the invention. If a term is not specifically defined herein, the meaning given to the term is that which one of ordinary skill would apply to the term within the context of the term's use.

The term "compound", as used herein, unless otherwise indicated, refers to any specific chemical compound disclosed herein, generally refers to β-D nucleoside analogs, but may include, within context, tautomers, regioisomers, geometric isomers, and where applicable, optical isomers (enantiomers) thereof, as well as pharmaceutically acceptable salts thereof, solvates and/or polymorphs. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds.

The term "patient" or "subject" is used throughout the specification to describe an animal, preferably a human, to whom treatment, including prophylactic treatment, with the compositions according to the present invention is provided. For treatment of those infections, conditions or disease states which are specific for a specific animal such as a human patient, the term patient refers to that specific animal. In general, in the present invention, the term patient refers to a human patient unless otherwise stated. In the present invention, in addition to humans, domesticated animals (e.g., horses, cows, dogs, cats, etc.) also may be commonly treated.

The term "H5N1 influenza" is used to describe a highly pathogenic subtype or strain of influenza A ("HPAI") originating in birds which is particularly lethal to humans.

Humans can be infected with influenza types A, B, and C viruses. Subtypes of influenza A that are currently circulating among people worldwide include H1N1, H1N2, and H3N2 viruses. Wild birds are the natural host for all known subtypes of influenza A viruses. Typically, wild birds do not become sick when they are infected with avian influenza A viruses. However, domestic poultry, such as turkeys and chickens, can become very sick and die from avian influenza, and some avian influenza A viruses also can cause serious disease and death in wild birds.

Avian influenza A virus strains are further classified as low pathogenic (LPAI) or highly pathogenic (HPAI) on the basis of specific molecular genetic and pathogenesis criteria that require specific testing. Most avian influenza A viruses are LPAI viruses that are usually associated with mild disease in poultry. In contrast, HPAI viruses can cause severe illness and high mortality in poultry. More recently, some HPAI viruses (e.g., H5N1) have been found to cause no illness in some poultry, such as ducks. LPAI viruses have the potential to evolve into HPAI viruses and this has been documented in some poultry outbreaks. Avian influenza A viruses of the subtypes H5 and H7,including H5N1, H7N7, and H7N3 viruses, have been associated with HPAI, and human infection with these viruses have ranged from mild (H7N3, H7N7) to severe and fatal disease (H7N7, H5N1).

In general, direct human infection with avian influenza viruses occurs very infrequently, and has been associated with direct contact (e.g., touching) infected sick or dead infected birds (domestic poultry).

The term "Venezuelan equine encephalitis virus" or "encephalomyletis (VEE) is a mosquito-borne viral pathogen that causes Venezuelan equine encephalitis or encephalomyletis (VEE). VEE can affect all equine species, such as horses, asses, and zebras. After infection, equines may suddenly die or show progressive central nervous system disorders. Humans also can contract this disease. Healthy adults who become infected by the virus may experience flu-like symptoms, such as high fevers and headaches. People with weakened immune systems and the young and the elderly can become severely ill or die from this disease.

The virus that causes VEE is transmitted primarily by mosquitoes that bite an infected animal and then bite and feed on another animal or human. The speed with which the disease spreads depends on the subtype of the VEE virus and the density of mosquito populations. Enzootic subtypes of VEE are diseases endemic to certain areas. Generally these serotypes do not spread to other localities. Enzootic subtypes are associated with the rodent-mosquito transmission cycle. These forms of the virus can cause human illness but generally do not affect equine health.

Epizootic subtypes, on the other hand, can spread rapidly through large populations. These forms of the virus are highly pathogenic to equines and can also affect human health. Equines, rather than rodents, are the primary animal species that carry and spread the disease. Infected equines develop an enormous quantity of virus in their circulatory system. When a blood-feeding insect feeds on such animals, it picks up this virus and transmits it to other animals or humans. Although other animals, such as cattle, swine, and dogs, can become infected, they generally do not show signs of the disease or contribute to its spread.

Serology testing has been performed on this virus and has shown the presence of six different subtypes (classified I to VI). There are seven different variants in subtype I, and three of these variants, A, B, and C are the epizootic strains. The present application relates to the treatment or prophylaxis (reducing the likelihood of prevention) of the six different subtypes and the variants within the subtypes.

The term "compound", as used herein, unless otherwise indicated, refers to any specific chemical compound disclosed herein and includes within the context of a compound's use, tautomers, regioisomers, geometric isomers, and where applicable, optical isomers thereof, as well as pharmaceutically acceptable salts, solvates and polymorphs thereof. Within its use in context, the term compound generally refers to a single compound, but also may include other compounds such as stereoisomers, regioisomers and/or optical isomers (including in some instances, racemic mixtures) as well as specific enantiomers or enantiomerically enriched mixtures of disclosed compounds. In aspects of the present invention, the β-D nucleoside analog is used, especially in a highly purified form.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of the phosphates according to the present invention.

The term "pharmaceutically acceptable derivative" is used throughout the specification to describe any pharmaceutically acceptable prodrug form (such as an ester, ether or amide or other prodrug group) which, upon administration to a patient, provides directly or indirectly the present compound or an active metabolite of the present compound.

The term "alkyl" shall mean within its context a $C_1$-$C_{20}$, preferably a $C_1$-$C_{10}$ linear, branch-chained or cyclic fully saturated hydrocarbon radical, which may be optionally substituted. The term "ether" shall mean an optionally substituted $C_1$ to $C_{20}$ ether group, formed from an oxygen and an alkyl group, or alternatively, may also contain at least one oxygen within the alkyl or alkylene chain.

The term "aromatic" or "aryl" shall mean within its context a substituted or unsubstituted monovalent carbocyclic aromatic radical having a single ring (e.g., phenyl) or multiple condensed rings (e.g., naphthyl, anthracene, phenanthrene). Other examples include optionally substituted heterocyclic aromatic ring groups ("heteroaromatic" or "heteroaryl") having one or more nitrogen, oxygen, or sulfur atoms in the ring. The preferred aryl group in compounds according to the present invention is a phenyl or a substituted phenyl group.

The term "heterocycle" shall mean an optionally substituted moiety which is cyclic and contains at least one atom other than a carbon atom, such as a nitrogen, sulfur, oxygen or other atom, which ring may be saturated and/or unsaturated.

The term "unsubstituted" shall mean substituted only with hydrogen atoms. The term "substituted" shall mean, within the chemical context of the compound defined, a substituent (each of which substituent may itself be substituted) selected from a hydrocarbyl (which may be substituted itself, preferably with an optionally substituted alkyl or fluoro group, among others), preferably an alkyl (generally, no greater than about 3 carbon units in length), including $CF_3$, an optionally substituted aryl, halogen (F, Cl, Br, I), thiol, hydroxyl, carboxyl, $C_1$-$C_3$ alkoxy, alkoxycarbonyl, CN, nitro or an optionally substituted amine (e.g. an alkyleneamine or a $C_1$-$C_3$ monoalkyl or dialkyl amine). Various optionally substituted moieties may be substituted with 3 or more substituents, preferably no more than 3 substituents and preferably with 1 or 2 substituents.

The term "acyl" is used throughout the specification to describe a group at the 5' position of the nucleoside analog (i.e., at the free hydroxyl position in the carbocyclic moiety) which contains a $C_1$ to $C_{20}$ linear, branched or cyclic alkyl chain. The acyl group at the 5' position, in combination with the 5' hydroxyl group results in an ester, which, after administration, may be cleaved to produce the free nucleoside form of the present invention. Acyl groups according to the present invention are represented by the structure:

where $R^4$ is a $C_1$ to $C_{20}$ linear, branched or cyclic alkyl group, alkoxyalkyl (including an ethylene oxide chain which may end in a free hydroxyl group or a $C_1$-$C_{10}$ alkyl group and ranges in molecular weight from about 50 to about 40,000 or about 200 to about 5,000), such as phenoxymethyl, aryl, alkoxy, alkoxycarbonyloxy groups (e.g., [(isopropoxycarbonyl)oxy]-methoxy), aryloxyalkyl,among others, all of which groups may be optionally substituted. Preferred acyl groups are those where $R^4$ is a $C_1$ to $C_{10}$ alkyl group. Acyl groups according to the present invention also include, for example, those acyl groups derived from benzoic acid and related acids, 3-chlorobenzoic acid, succinic, capric and caproic, lauric, myristic, palmitic, stearic and oleic groups, among numerous others and may include such related groups as sulfone groups such as mesylate groups. All groups may be appropriately substituted within context as otherwise described herein. One of ordinary skill in the art will recognize the acyl groups which will have utility in the present invention, either to synthesize the target pharmaceutical compounds or as prodrug of the nucleosides according to the present invention.

The term "amino acid" or "amino acid residue" shall mean, within context, a radical of a D- or L-amino acid which is covalently bound to a nucleoside analog at the 4' exocyclic amine position of the cytosine base or the 5'- or 3'-OH position of the sugar synthon ($R^2$, $R^1$ or $R^{1a}$) through a carboxylic acid moiety of the amino acid, thus forming respectively, an amide or ester group linking the nucleoside to the amino acid. Representative amino acids include both natural and unnatural amino acids, preferably including, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine, among others.

The term "phosphate ester" or "phosphodiester" is used throughout the specification to describe mono-phosphate groups at the 5' position of the carboyclic sugar synthon which are mono- or diesterified such that the phosphate group is negatively charged or is rendered neutral, i.e., has a neutral charge. Phosphate esters for use in the present invention include those represented by the structures:

where each $R^5$, $R^6$ and $R''$ is independently selected from H, a $C_1$ to $C_{20}$ linear, branched or cyclic alkyl group, alkoxyalkyl, aryloxyalkyl, such as phenoxymethyl, aryl and alkoxy, among others, including alkoxycarbonyloxy groups (e.g., (isopropoxycarbonyl)oxy]-methoxy) with the proviso that at least one $R^5$ group is other than H, or the two $R^5$ groups together form a five- or six-membered heterocyclic group, B is a direct bond (N directly bonded to C of the ester/carboxylic acid group) or a $C_1$-$C_3$ alkylene group optionally substituted with a $C_1$-$C_3$ alkyl group, preferably a methyl group and $R^7$ is a $C_1$ to $C_{20}$ linear, branched or cyclic alkyl or acyl group, alkoxyalkyl, aryloxyalkyl, such as phenoxymethyl, aryl and alkoxy, among others, each of which groups previously mentioned may be optionally substituted. Preferred monophosphate esters for use in prodrug forms according to the present invention are those where $R^5$ is a $C_1$ to $C_{20}$ linear or branched chain alkyl group, more preferably a $C_1$ to $C_3$ alkyl group, all of which groups may be optionally substituted.

The term "effective amount" shall mean an amount or concentration of a compound according to the present invention which is effective within the context of its administration, which may be inhibitory, prophylactic and/or therapeutic. Within context, all active compounds which are used in the present invention are used in effective amounts. The present compound also relates to combinations of compounds which contain effective amounts of each of the compounds used, whether that combination is additive or synergistic in effect, provided that the overall effect of the combination of compounds is to inhibit the growth, reduce the likelihood of or treat viral infections in patients.

The term "D-configuration" as used in the context of the present invention refers to the configuration of the nucleoside compounds according to the present invention which mimics the natural configuration of sugar moeties as opposed to the unnatural occurring nucleosides or "L" configuration. The term "β" or "β anomer" is used to describe nucleoside analogs according to the present invention in which the nucleoside base (in this case cytosine or 5-fluorocytosine) is configured (disposed) above the plane of the carbocyclic moiety in the carbodine or 5-fluoro carbodine analog.

The term "enantiomerically enriched" is used throughout the specification to describe a nucleoside which includes at least about 95%, preferably at least about 96%, more preferably at least about 97%, even more preferably, at least about 98%, and even more preferably at least about 100% or more of a single enantiomer of that nucleoside. Carbodine and 5-F carbodine compounds according to the present invention are generally β-D-nucleoside compounds. When the present carbodine compounds according to the present invention are referred to in this specification, it is presumed that the nucleosides have the D-nucleoside configuration and are enantiomerically enriched (preferably, about 100% of the D-nucleoside), unless otherwise stated.

The terms "coadminister" and "coadministration" are used synonymously to describe the administration of at least one of the carbodine or 5-F carbodine nucleoside compounds according to the present invention in combination with at least one other agent, preferably at least one additional anti-viral agent (such as oseltamavir phosphate or tamiflu), including other nucleoside anti-viral agents which are specifically disclosed herein in amounts or at concentrations which would be considered to be effective amounts at or about the same time. While it is preferred that coadministered agents be administered at the same time, agents may be administered at times such that effective concentrations of both (or more) agents appear in the patient at the same time for at least a brief period of time. Alternatively, in certain aspects of the present invention, it may be possible to have each coadministered agent exhibit its inhibitory effect at different times in the patient, with the ultimate result being the inhibition of influenza A, especially H5N1 influenza or VEE and the treatment of the aforementioned infections. Of course, when more than one viral or other infection or other condition is present, the present compounds may be combined with agents to treat that other infection or condition as required.

The term "independently" is used herein to indicate that the variable, which is independently applied, varies independently from application to application.

The present invention relates to carbocyclic nucleoside compounds according to the structure:

Wherein R is H or F;
$R^1$ and $R^{1a}$ are each independently H, an acyl group, a $C_1$-$C_{20}$ alkyl or ether group, a phosphate, diphosphate, triphosphate or phosphodiester group or together $R^1$ and $R^{1a}$ form a carbodiester or phosphodiester group with the oxygen atoms to which they are bonded;
$R^2$ is H, an acyl group, a $C_1$-$C_{20}$ alkyl or ether group;
And pharmaceutically acceptable salts, enantiomers, hydrates and solvates thererof.

In certain aspects of the invention, $R^{1a}$ is H. Also, in certain aspects of the invention, $R^1$ and $R^2$ are both H. R is preferably H.

The present invention also relates to pharmaceutical compositions comprising an effective amount of a compound as described above, optionally in combination with a pharmaceutically acceptable carrier, additive or excipient.

Methods of treatment represent further embodiments according to the present invention. In this aspect a method of treating or reducing the likelihood of an Avian influenza A infection, in particular, a H5N1 strain viral infection or a Venezuelan equine encephalitis viral infection in a patient comprising administering to a patient in need of therapy or at risk for infection thereof an effective amount of a compound as otherwise described above.

Chemical Synthesis

Compositions according to the present invention are synthesized readily from D-ribose according to scheme I, which is presented below. In this scheme, D-ribose is first converted through a series of chemical steps to a protected carbocyclic five-membered ring as depicted below (comp -continued Reagents and conditions: (a) 2, 2-DMP, p-toluenesulfonic acid, acetone, 0° C. to rt, 2 h; (b) TBDMSCl, imidazole, CH$_2$Cl$_2$, rt, 4 h; (c) vinylmagnisium bromide, THF, -78° C. to rt, 2 h; (d) TBAF, THF, rt, 2 h; (e) NaIO$_4$, H$_2$O, rt, 2 h; (f) KO$^t$Bu, methyltriphenylphosphonium bromide, THF, 0° C. to rt, 6 h; (g) 1$^{st}$ gen. Grubb's catalyst, CH$_2$Cl$_2$, rt, 7 h; (h) PDC, 4 A° molecular sieves, AcOH, CH$_2$Cl$_2$, rt, 12 h; (i) (t-BuOCH$_2$)$_2$CuLi, t-BuOMe/THF, -30° C., 30 min; (j) CECl$_3$7H$_2$O, NaBH$_4$, MeOH, -78° C. to rt, 1 h; (k) MsCl, Et$_3$N, CH$_2$Cl$_2$, 0° C., 1 h; (l) NaN$_3$, DMF, 140° C., 4 h; (m) 10% Pd/C, EtOH, rt, 30 psi, 5 h; (n) β-methoxyacryloyl isocyanate, DMF, -20° C. to rt, 10 h; (o) 30% NH$_4$OH, EtOH/dioxane (1:1), 100° C., 20 h; (p) 2, 4, 6-triisopropylbenzenesulfonyl chloride, DMAP, Et$_3$N, 30% NH$_4$OH, rt,12 h; (q) TFA/H$_2$O (2:1), 60° C., 4 h; (r) Ac$_2$O, Et$_3$N, DMAP, CH$_3$CN, rt, 30 min; (s) i. selectfluor, AcOH, CH$_3$CN, 95° C., 3 h; ii. Et$_3$N, 95° C., 3 h.

Pharmaceutical compositions based upon the nucleoside compounds according to the present invention comprise one or more of the above-described compounds in a therapeutically effective amount for treating a viral, especially an Avian Influenza A strain viral infection, in particular, a H5N1 viral infection or a Venezuelan equine encephalitis (VEE) infection in a patient in need of therapy thereof, optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacokinetics of the agent used, as well as the patient or subject (animal or human) to be treated.

In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, subcutaneous, suppository or other route. Intravenous and intramuscular formulations are preferably administered in sterile saline. In certain instances, transdermal administration may be preferred. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) and ether (alkyl and related) derivatives, phosphate esters and various salt forms of the present compounds, are preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within therapeutically active formulations according to the present invention is an effective amount for treating the infection or condition, especially an Avian influenza A infection, in particular, a H5N1 strain viral infection or a Venezuelan equine encephalitis viral infection. In general, a therapeutically effective amount of the present compound in pharmaceutical dosage form usually ranges from about 0.05 mg/kg to about 100 mg/kg per day or more, more preferably, slightly less than about 1 mg/kg to about 25 mg/kg per day of the patient or considerably more, depending upon the compound used, the condition or infection treated and the route of administration. The active nucleoside compound according to the present invention is preferably administered in amounts ranging from about 0.5 mg/kg to about 25 mg/kg per day of the patient, depending upon the pharmacokinetics of the agent in the patient. This dosage range generally produces effective blood level concentrations of active compound which may range from about 0.05 to about 100 micrograms/cc of blood in the patient. For purposes of the present invention, a prophylactically or preventive effective amount of the compositions according to the present invention falls within the same concentration range as set forth above for therapeutically effective amount and is usually the same as a therapeutically effective amount.

Administration of the active compound may range from continuous (intravenous drip) to several oral administrations per day (for example, Q.I.D.) or transdermal administration and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the bioavailability/pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly enhance the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In particularly preferred embodiments according to the present invention, the compounds and compositions are used to treat, prevent or delay the onset of an Avian influenza A infection, in particular, a H5N1 strain viral infection or a Venezuelan equine encephalitis viral infection. Preferably, to treat, prevent or delay the onset of these infections, the compositions will be administered in oral dosage form in amounts ranging from about 250 micrograms up to about 500 mg or more at least once a day, preferably, up to four times a day. The present compounds are preferably administered orally, but may be administered parenterally, topically or in suppository form.

In the case of the co-administration of the present compounds in combination with an another compound used to treat an Avian influenza A infection, in particular, a H5N1 strain viral infection and/or a Venezuelan equine encephalitis viral infection, such as Tamiflu, the amount of the carboline or 5-fluorcarboline nucleoside compound to be administered ranges from about 1 mg/kg. of the patient to about 500 mg/kg. or more of the patient or considerably more, depending upon the second agent to be co-administered and its potency against influenza (e.g. H5N1) or the VEE virus to be inhibited, the condition or infection treated and the route of administration. In the case of influenza A (e.g. H5N1 infections) the other agent may be preferably administered in amounts ranging from about 100 ug/kg (micrograms per kilogram) to about 500 mg/kg. In certain preferred embodiments, these compounds may be preferably administered in an amount ranging from about 1 mg/kg to about 50 mg/kg or more (usually up to about 100 mg/kg), generally depending upon the pharmacokinetics of the two agents in the patient. These dosage ranges generally produce effective blood level concentrations of active compound in the patient.

The compounds according to the present invention, may advantageously be employed prophylactically to prevent or reduce the likelihood of a viral infection or to prevent or reduce the likelihood of the occurrence of clinical symptoms associated with the viral infection or to prevent or reduce the likelihood of the spread of a viral infection to another person. Thus, the present invention also encompasses methods for the prophylactic treatment of an avian influenza A strain (e.g. H5N1) viral infection or a VEE viral infection. In this aspect according to the present invention, the present compositions are used to prevent, reduce the likelihood of or delay the onset of a viral infection or a virus related disease or condition or the spread of infection to other people. This prophylactic method comprises administering to a patient in need of such treatment or who is at risk for the development of an avian influenza A strain (e.g. H5N1) viral infection or a VEE viral infection or an infected patient who wishes to prevent or reduce the likelihood of a viral infection from spreading to another person, an amount of a compound according to the present invention alone or in combination with another antiviral effective for alleviating, preventing or delaying the onset of the viral infection. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of compounds of the present invention for the prophylactic treatment of viral infections, these compounds may be administered within the same dosage range for therapeutic treatment (i.e., about 250 micrograms up to about 500 mg. or more from one to four times per day for an oral dosage form) as a prophylactic agent to prevent the proliferation of the viral infection or alternatively, to prolong the onset of or reduce the likelihood of a patient contracting a virus infection which manifests itself in clinical symptoms.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Experimental (Chemical Synthesis)

2,3-O-Isopropylidene-D-ribofuranose (1). A suspension of D-ribose (300 g, 1.99 mol) in acetone (3000 mL) was cooled to 0° C. and treated with p-toluenesulfonic acid (11.4 g, 0.059 mol) and 2,2-dimethoxypropane (268 mL, 2.19 mol). After stirred at room temperature for 2 h, the clear resulting mixture was neutralized with $NaHCO_3$ (6.7 g), filtered and the filtrate was concentrated in vacuo. The residue was purified by silica gel column chromatography (EtOAc:hexane=1:2) to afford 1 (342 g, 90%) as a colorless oil. $^1$H NMR ($CDCl_3$) δ 5.62 (s, 1H), 4.83 (d, J=5.9 Hz, 1H), 4.73 (d, J=5.9 Hz, 1H), 4.41 (s, 1H), 3.72 (m, 2H), 1.48 (s, 3H), 1.32 (s, 3H); $^{13}$C NMR ($CDCl_3$) δ 112.05, 102.61, 87.53, 86.60, 81.53, 63.37, 26.23, 24.58.

5-(tert-Butyldimethylsilyloxy)-2,3-isopropylidenedioxy-D-ribofuranose (2). A solution of 1 (320 g, 1.68 mol) in $CH_2Cl_2$ (3000 mL), tert-Butyldimethylsilyl chloride (304 g, 2.01 mol) and imidazole (172 g, 2.52 mol) were added at 0° C. After stirred for 4 h at room temperature, $H_2O$ (1000 mL) was added to the reaction mixture. The water layer was separated and the organic layer was dried over $Na_2SO_4$ and filtered. The filtrate was concentrated in vacuo and the residue was purified by column chromatography on a silica gel (EtOAc:hexane=1:20) to give 2 (415 g, 81%) as a colorless oil. $^1$NMR ($CDCl_3$) δ 5.27 (d, J=11.7 Hz, 1H), 4.77 (d, J=11.8 Hz, 1H), 4.69 (d, J=5.9 Hz, 1H), 4.49 (d, J=5.9 Hz, 1H), 4.35 (s, 1H), 1.54 (s, 0.3H), 1.47 (s, 2.7H), 1.38 (s, 0.3H), 1.31 (s, 2.7H), 0.92 (s, 8H), 0.87(s, 1H), 0.16 (d, J=2.8 Hz, 0.6H), 0.13 (d, J=2.8 Hz, 5.4H); $^{13}$C NMR ($CDCl_3$) δ 112.00, 103.59, 103.43, 97.94, 88.70, 87.98, 87.58, 86.94, 81.87, 81.73, 81.18, 79.39, 65.47, 64.78, 63.83, 26.44, 25.74, 25.51, 24.89, −5.72.

(4R,5S)-1-{4-[2-(tert-Butyldimethylsilyloxy)-1-hydroxyethyl]-2,2-dimethyl-1,3-dioxolan-5-yl}-(S)-prop-2-en-1-ol (3). A solution of 2 (250 g 0.82 mol) in anhydrous tetrahydrofuran (1700 mL) was cooled to −78° C. and vinylmagnesium bromide (1M solution in tetrahydrofuran, 2.62 L, 2.62 mol) was added dropwise under −78° C. After addition was completed, the reaction mixture was allowed to stir at room temperature for 2 h. The reaction mixture was poured in to a mix of saturated $NH_4Cl$ (aq) and ether (1:2) (3 L). The organic and layer was separated and aqueous layer was extracted with ether (2 x 600 mL). The combined organic layers was washed with brine, dried over $MgSO_4$, filtered and concentrated in vacuo. The residue was purified by silica gel column chromatography (EtOAc:hexane=1:20) to give 3 (251 g, 92%) as colorless oil. $[α]^{23}_D$+6.86° (C 0.59, $CHCl_3$); $^1$H NMR (400 MHz, $CDCl_3$) δ 6.02 (m, 2H), 5.43 (d, J=17.2 Hz, 1H), 5.26 (d, J=10.4 Hz, 1H), 4.35 (bs, OH, $D_2O$ exchangeable, 1H), 4.31 (bs, 1H), 4.07 (m, 2H), 3.86 (m, 2H), 3.65 (dd, J=6.7 and 9.9 Hz, 1H), 3.36 (bs, OH, $D_2O$ exchangeable, 1H), 1.39 (s, 3H), 1.32(s, 3H), 0.91 (s, 9H), 0.10 (s, 6H); $^{13}$C NMR (100 MHz, $CDCl_3$) δ 137.31, 115.93, 108.65, 80.62, 76.53, 69.61, 69.22, 64.14, 27.86, 25.73, 25.29, −5.53; Anal. Calcd for $C_{16}H_{32}O_5Si$: C, 57.79; H, 9.70. Found: C, 58.13; H, 9.80.

(4R,5S)-1-[4-(1,2-dihydroxyethyl)-2,2-dimethyl-[1,3]dioxolan-5-yl]-(S)-prop-2-en-1-ol (4). Tetrabutylammonium fluoride (1 M solution in tetrahydrofuran, 1128 mL, 1.12 mol) was added to a solution of 3 (250 g, 0.75 mol) in tetrahydrofuran (1000 mL) and stirred at room temperature for 2 hr. The resulting brown mixture was concentrated in vacuo and the residue was purified by column chromatography on a silica gel (EtOAc:Hexane=2:1) to give 4 (161 g, 98%) as a white solid. mp 73-74° C.; $[α]^{23}_D$−31.33° (C. 1.00, $CHCl_3$); $^1$H NMR (400 MHz, $CDCl_3$) δ 6.03 (m, 1H), 5.40 (dd, J=0.8 and 17.2 Hz, 1H), 5.31 (dd, J=0.8 and 10.5 Hz, 1H), 4.34 (t, J=8.1 Hz, 1H), 4.16 (dd, J=5.4 and 9.4 Hz, 1H), 4.06 (dd, J=5.4 and 9.2 Hz, 1H), 3.95-3.87 (m, 1H $D_2O$ exchangeable, 3H), 2.15 (bs, OH, $D_2O$ exchangeable, 1H), 1.40 (s, 3H), 1.34(s, 3H); $^{13}$C NMR (100 MHz, $CDCl_3$) δ 137.64, 117.13, 79.98, 77.83, 69.31, 64.56, 27.96, 25.43; Anal. Calcd for $C_{10}H_{18}O_5$.0.03 hexane: C, 55.37; H, 8.41. Found: C, 55.60; H, 8.31.

(1S,2S,3S)-2,2-Dimethyl-6-vinyltetrahydrofuro[3,4,d]-1,3-dioxol-4-ol (5). A triol 4 (161 g, 737.6 mmol) in $H_2O$ (1600 mL) was cooled to 0° C. and $NaIO_4$ (237 g, 1.106 mol) was added portion wise. After stirring at room temperature for 2 h, the reaction mixture was extracted with EtOAc (500 mL×3) and the extracts were dried over $MgSO_4$, filtered, and concentrated to dryness under reduced pressure. The residue was purified by silica gel column chromatography (EtOAc:hexane=1:10) to give 5 (129 g, 94%) as a colorless oil. $^1$H NMR (400 MHz, $CDCl_3$) δ 6.01 (m, 0.8H), 5.79 (m, 0.2H), 5.50 (d, J=2.8 Hz, 0.8H), 5.43-5.16 (m, 2.2H), 4.70-4.56 (m, 3H), 3.93 (d, J=10.4 Hz, 0.2H), 2.66 (d, J=2.8 Hz, 0.8H), 1.59 (s, 0.6H), 1.51 (s, 2.4H), 1.39 (s, 0.6H), 1.33 (s, 2.4H); $^{19}$C NMR (100 MHz, CDCl$_3$) δ 137.94, 134.43, 117.31, 117.01, 114.32, 112.45, 102.95, 102.91, 96.15, 88.54, 86.62, 84.73, 80.58, 79.01, 26.42, 26.19, 24.95; Anal. Calcd for C$_9$H$_{14}$O$_4$: C, 58.05 H, 7.58. Found: C, 58.38; H, 7.74.

(1S,2S,3R)-1-(2,2-Dimethyl-5-vinyl[1,3]dioxolan-4-yl)-(S)-prop-2-en-1-ol (6). A suspension of methyltriphenylphosphonium bromide (562 g, 1.55 mol) in tetrahedrofuran (1000 mL) was cooled to 0° C. and KO'Bu (210 g, 1.86 mol) was added portion wise under nitrogen atmosphere. The reaction mixture was stirred at room temperature for 2 h and then recooled to 0° C. A solution of lactol 5 (116 g, 0.622 mol) in tetrahydrofuran (300 mL) was added to the resulting reaction mixture at 0° C. The mixture was stirred for 6 h at rt, diethyl ether (1500 mL) was added to the reaction mixture, and washed with H$_2$O (500 mL) and brine (500 mL). The organic layer was dried over MgSO$_4$, filtered and concentrated in vacuo. The residue was purified by silica gel column chromatography (EtOAc:hexane=1:10) to give 6 (101 g, 88%) as a colorless oil. $^1$H NMR (400 MHz, CDCl$_3$) δ 6.05 (m, 2H), 5.36 (m, 4H), 4.70 (t, J=6.8 Hz, 1H), 4.19 (m, 1H), 4.04 (dd, J=6.8 and 7.6 Hz, 1H), 1.79 (bs, 1H), 1.50 (s, 3H), 1.38 (s, 3H); $^{13}$C NMR (100 MHz, CDCl$_3$) δ 137.89, 134.24, 118.47, 116.63, 109.06, 80.72, 78.88, 71.20, 27.80, 25.46; Anal. Calcd for C$_{10}$H$_{16}$O$_3$: C, 65.19; H, 8.75. Found: C, 65.34; H, 8.43.

(4R,5R)-4.5-O-Isopropylidene-cyclopent-2-enone (7). To a solution of first generation Grubb's catalyst (4.198 g, 5.10 mmol, 1 mol%) in anhydrous CH$_2$Cl$_2$ (300 mL), diene 6 (94 g, 510.2 mmol) in anhydrous CH$_2$Cl$_2$ (1500 mL) was added and stirred for 7 h at rt under nitrogen atmosphere. To the mixture 4 Å molecular sieves (94 g), pyridinium dichromate (288 g, 765.3 mmol) and acetic acid (1.53 mL, 25.5 mmol) were added. The resulting brown mixture was stirred at rt for 12 h and filtered through a celite pad with CH$_2$Cl$_2$. The filtrate was concentrated in vacuo and the residue was purified by column chromatography on a silica gel (EtOAc:hexane=1:10) to give 7 (72 g, 91%) as a white crystalline solid. mp 68.5-70.3° C.; [α]$^{23}_D$ –69.3 (c 0.60, CHCl$_3$); $^1$H NMR (400 MHz, CDCl$_3$) δ 7.61 (dd, J=2.4, 6.0 Hz, 1H), 6.22 (d, J=6.0 Hz, 1H), 5.28 (dd, J=2.4, 5.6 Hz, 1H), 4.47 (d, J=5.6 Hz, 1H), 1.42 (s, 3H), 1.41 (s, 3H); $^{13}$C NMR (100 MHz, CDCl$_3$) δ 159.56, 134.64, 115.36, 78.58, 76.49, 27.40, 26.14; Anal. Calcd for C$_{10}$H$_{10}$O$_3$: C, 62.33; H, 6.54. Found: C, 62.15; H, 6.52.

(1S,2S,3R,4R)-4-(tert-Butoxymethyl)-2,3-(isopropylidenedioxy)-1-cyclopentanone (8). A suspension of potassium tert-butoxide (41.6 g, 0.35 mol) in anhydrous tert-butylmethyl ether (1200 ml) was cooled to –78° C. under nitrogen. The well stirring mixture was treated with sec-butyllithium (1.6 M solution in hexane, 250 mL, 0.35 mol) over 20 min. After the mixture was stirred for 2 h at –78° C., a solution of LiBr (61 g, 0.70 mol) in THF (450 mL) was added drop wise over 20 min at –78° C. and the resulting solution was stirred at –15° C. for 30 min. Upon recooling to –78° C., a solution of CuBr.SMe$_2$ (37.3 g, 0.14 mol) in diisopropyl sulfide (150 mL) was added drop wise over 20 min. The resulting viscous dark solution was stirred for 1 h at –78° C. and treated with a solution of enone 7 (18.1 g, 0.117 mol) in THF (150 mL) over 15 min. The reaction mixture was allowed to warm to –30° C. over 15 min and stirred for 30 min at –30° C. The mixture was recooled to –78° C. and 1:1 acetic acid-methanol (415 mL) was added and the mixture poured in to 3000 mL of NH$_4$Cl/NH4OH (1:1). After removal of the aqueous layer, the organic layer was washed with a saturated aqueous NH$_4$Cl solution (300 mL×2) and brine (400 mL). The organic phase was dried (Na$_2$SO4), filtered, concentrated and purified through silica gel column chromatography with 5% EtOAc in hexanes to give 8 (25 g, 88%) as a white solid. NMR (500 MHz, CDCl$_3$) δ 1.10 (s, 9H), 1.34 (s, 3H), 1.43 (s, 3H), 2.06 (d, J=22 Hz, 1H), 2.55 (d, J=12.5 Hz, 1H), 2.72 (dd, J=11, 22 Hz, 1H), 3.34 (dd, J=3.5, 10.5 Hz, 1H), 3.52 (dd, J=3.5, 10.5 Hz, 1H), 4.22 (d, J=7 Hz, 1H), 4.61 (d, J=7 Hz, 1H); Anal. Calcd for C$_{13}$H$_{22}$O$_4$: C, 64.44; H, 9.15. Found: C, 64.19; H, 9.14.

(1S,2S,3R,4R)-4-(tert-Butoxymethyl)-2,3-(isopropylidenedioxy)-cyclopentan-1-ol (9). A solution of compound 8 (25 g, 0.103 mol) and CeCl$_3$.7H$_2$O (49.96 g, 0.134 mol) in MeOH (200 mL) was stirred 15 min at rt. The mixture was cooled to –78° C., NaBH$_4$ (5.07 g, 0.134 mol) was slowly added and allowed the mix warm to 0° C. After stirring 1 h at 0° C., cold water (20 mL) was added and the methanol was removed under reduced pressure. The residue was extracted with EtOAc (2×600 mL), the combined organic phase was washed with brine (500 mL) and then dried over anhydrous Na$_2$SO$_4$, and filtered. The solvent was evaporated under reduced pressure and the residue was purified by silica gel column chromatography (15% EtOAc:hexane) to give 9 (24 g, 95%) as a syrup. [α]$^{26}_D$ –16.95 (c 1.59, CHCl$_3$); $^1$H NMR (400 MHz, CDCl$_3$) δ 1.13 (s, 9H), 1.34 (s, 3H), 1.48 (s, 3H), 1.83 (m, 2H), 2.19 (m, 1H), 2.44 (d, J=9.0 Hz, 1H, D$_2$O exchangeable), 3.20 (dd, J=4.5, 8.8 Hz, 1H), 3.31 (dd, J=4.5, 8.8 Hz, 1H), 4.23 (m, 1H), 4.44 (m, 2H); Anal. Calcd for C$_{13}$H$_{24}$O$_4$; C, 63.91; H, 9.90. Found: C, 64.09; H, 9.87.

(1S,2S,3R,4R)-4-(tert-Butoxymethyl)-2,3-(isopropylidenedioxy)-1-(methylsulfonyloxy)-cyclopentane (10). A miture of compound 9 (22 g, 90.04 mmol) and triethylamine (37.4 mL, 270.14 mmol) in CH$_2$Cl$_2$(400 mL), methane sulfonyl chloride (10.41 mL, 135.07 mmol) was added drop wise at 0° C. After stirring for 1 h at 0° C., the reaction mixture was quenched with cold water (300 mL) and extracted with CH$_2$Cl$_2$ (2×500 mL). The combined organic layers were washed with brine (400 mL) and dried over anhydrous Na$_2$SO$_4$, filtered, concentrated under reduced pressure and purified using column chromatography with EtoAc:hexane (1:1) to give 10 (quantitative yield) as a colorless oil.

(1R,2S,3R,4R)-1-Azido-4-(tert-butoxymethyl)-2,3-(isopropylidenedioxy)-cyclopentane (11). A solution of 10 (30 g, 93.04 mmol) in dry DMF (400 mL) in the presence of sodium azide (60.49 g, 930.4 mmol) was heated at 140° C. for 5 h with stirring. After cooling to room temperature, the reaction mixture was filtered, and the filtrate was concentrated to dryness. The residue was diluted with EtOAc (500 mL), washed with water (2×300 mL) and brine (200 mL). The organic layer was dried over Na$_2$SO$_4$, filtered and concentrated to dryness. The resulting oil was purified by silica gel column chromatography (4% EtOAc in hexane) to give 11 (22.2 g, 89%) as a colorless oil. [α]$^{26}_D$ –46.94° (c 1.11, CHCl$_3$); $^1$H NMR (400 MHz, CDCl$_3$) δ 1.18 (s, 9H), 1.30 (s, 3H), 1.46 (s, 3H), 1.71 (m, 1H), 2.29 (m, 2H), 3.29 (dd, J=6.7, 8.8 Hz, 1H), 3.37 (dd, J=7.0, 8.8 Hz, 1H), 3.96 (m, 1H), 4.40 (dd, J=2.3, 6.1 Hz, 1H), 4.48 (dd, J=2.0, 6.1 Hz, 1H); Anal. Calcd for C$_{13}$H$_{23}$N$_3$O$_3$.0.13EtOAc: C, 57.95; H, 8.65; N, 14.99. Found: C, 58.25; H, 8.71; N, 14.76.

(1R,2S,3R,4R)-4-(tert-Butoxymethyl)-2,3-(isopropylidenedioxy)-1-cyclopentanamine (12). A suspension of compound 11 (20 g) and 10% Pd/C (5.0 g) in absolute EtOH (250 mL) was shaken under 35 psi of H$_2$ for 5 h. The reaction mixture was filtered and the filtrate was evaporated to give crude 12 (quantitative yield) which was used for next step without further purification. $^1$H NMR (400 MHz, CDCl$_3$) δ 1.18 (s, 9H), 1.28 (s, 3H), 1.36 (m, 1H), 1.45 (s, 3H), 1.89 (br s, 2H, NH$_2$), 2.24-2.36 (m, 2H), 3.34-3.43 (m, 3H), 4.21 (dd, J=2.6, 6.2 Hz, 1H), 4.48 (dd, J=2.8, 6.2 Hz, 1H); Anal. Calcd for C$_{13}$H$_{25}$NO$_3$.0.16H$_2$O: C, 63.41; H, 10.37; N, 5.69. Found: C, 63.09; H, 10.16; N, 5.59.

N-{[(1R,2S,3R,4R)-4-(tert-Butoxymethyl)-2,3-(isopropylidenedioxy)-cyclopentyl]-aminocarbonyl}-3-methoxy-2-propenamide (13). A solution of β-methoxy acrylic acid in a mixture of $CH_2Cl_2$: benzene (2:1) (600 mL) was cooled to 0° C., then anhydrous DMF (1.2 mL) was added followed by oxalyl chloride (90 mL) was added at 0° C. under nitrogen atmosphere. The mix was stirred at 0° C. for 1 h and the solution was concentrated under reduced pressure to give the crude β-methoxy acryloyl chloride. Silver cyanate (77 g) was added to a solution of above obtained crude β-methoxy acryloyl chloride in anhydrous benzene (300 mL). The resulting mixture was heated under reflux for 1 h and allowed to cool to room temperature. After the solid phase had settled, the supernatant solution was contained with β-methoxy acryloyl isocyanate was added during 15 min to a solution of amine 12 (18 g) in anhydrous DMF (50 mL) at −15 to −20° C. under nitrogen. The reaction mixture was stirred for 2 h at −15° C. and then for 10 h at room temperature under nitrogen. The solvent was removed under reduced pressure and purified using silica gel column chromatography to afford 13 (19.8 g, 72%) as a solid. $[α]^{27}_D$ −26.62 (c 0.57, $CHCl_3$); $^1H$ NMR (400 MHz, $CDCl_3$) δ 1.17 (s, 9H), 1.28 (s, 3H), 1.47 (s, 3H), 1.58 (m, 1H), 2.28 (m, 1H), 2.36-2.43 (m, 1H), 3.33-3.42 (m, 2H), 3.73 (s, 1H), 4.20 (m, 1H), 4.45 (m, 2H), 5.35 (d, J=12.3 Hz, 1H), 7.67 (d, J=12.3 Hz, 1H), 8.72 (br s, 1H, NH), 9.35 (br s, 1H, NH); Anal. Calcd for $C_{18}H_{30}N_2O_6$: C, 58.36; H, 8.16; N, 7.56. Found: C, 58.28; H, 8.13; N, 7.60.

(1R,2S,3R,4R)-1-[4-(tert-Butoxymethyl)-2,3-(isopropylidenedioxy)-cyclopentan-1-yl]-uracl (14). Compound 13 (18 g, 11.34 mmol) was dissolved in ethanol (80 mL), dioxane (60 mL) and ammonium hydroxide (30%, 80 mL). The reaction mixture was heated at 100° C. in a steel bomb for 20 h. After cooling, the solution was evaporated to dryness. The residue was purified by silica gel column chromatography (50% EtOAc in hexane) to give 14 (14 g, 85%) as a white foam. $[α]^{27}_D$ −41.53 (c 0.88, $CHCl_3$); UV (MeOH) $λ_{max}$ 266.0 nm; $^1H$ NMR (400 MHz, $CDCl_3$) δ 1.19 (s, 9H), 1.30 (s, 3H), 1.54 (s, 3H), 1.97 (m, 1H), 2.32-2.41 (m, 2H), 3.43-3.50 (m, 2H), 4.48 (dd, J=4.1, 6.5 Hz, 1H), 4.65-4.75 (m, 2H), 5.72 (d, J=8.0 Hz, 1H), 7.35 (d, J=8.0 Hz, 1H), 8.63 (br s, 1H, NH); Anal. Calcd for $C_{17}H_{26}N_2O_5$: C, 60.34; H, 7.74; N, 8.28. Found: C, 60.06; H, 7.70; N, 8.14.

(1R,2S,3R,4R)-1-[4-(tert-Butoxymethyl)-2,3-(isopropylidenedioxy)-cyclopentan-1-yl]-cytosine (15). A mixture of 14 (8 g, 23.6 mmol) and 4-dimethylamino-pyridine (5.78 g, 47.3 mmol) in anhydrous acetonitrile (250 mL), triethylamine (6.59 mL, 47.3 mmol) followed by 2,4,6-triisopropylbenzenesulfonyl chloride (14.33 g, 47.3 mmol) was added at rt under nitrogen. After being stirred for 12 h, $NH_4OH$ (30%, 200 mL) was added and stirred for 5 hours. The mixture was diluted with chloroform and washed with saturated aqueous $NH_4Cl$ (3×600 mL) solution and followed by washed with water (3×600 mL). The organic layer was dried over $Na_2SO_4$, filtered and concentrated under reduced pressure. The residue was purified using silica gel column chromatography ($CH_2Cl_2$:MeOH=96:4) to give 15 (6.22 g, 78%) as a solid. UV (MeOH) $λ_{max}$ 275.0 nm; $^1H$ NMR (500 MHz, DMSO-$d_6$) δ 1.14 (s, 9H), 1.22 (s, 3H), 1.44 (s, 3H), 1.80 (m, 1H), 2.10 (m, 2H), 3.30 (dd, J=6, 9 Hz, 1H), 3.40 (d, J=5.5, 9.5 Hz, 1H), 4.38 (dd, J=5, 7 Hz, 1H), 4.60 (m, 1H), 4.75 (dd, J=5, 6.5 Hz, 1H), 5.71 (d, J=7.5 Hz, 1H), 7.13 (brs, 1H), 7.22 (brs, 1H), 7.70 (d, J=7.5 Hz, 1H); Anal. Calcd for $C_{17}H_{27}N_3O_4$: C, 60.51; H, 8.07; N, 12.45. Found: C 60.42; H 8.03; N 12.45.

(1R,2S,3R,4R)-1-[2,3-Dihydroxy-4-(hydroxymethyl)-cyclopentan-1-yl]cytosine (16). Compound 15 (5.5 g) was dissolved in $CF_3CO_2H/H_2O$ (2:1) (150 mL) and heated to 70° C. for 4 h. The solution was then concentrated under reduced pressure and coevaporated three times with methanol (3×200 mL). The residue was dissolved in water (300 mL) and washed with $CH_2Cl_2$ (4×100 mL). The water layer was concentrated under vacuum and the residue was dissolved in methanol and neutralized with IRA-400 (OH) basic resin. The resin was filtered, washed with methanol and the filtrate was concentrated under reduced pressure to give 16 (2.75 g, 82%) as a white solid. mp 214° C.; $[α]^{27}_D$ −74.5 (c 0.52, $H_2O$); UV ($H_2O$) $λ_{max}$ 275.0 nm (pH 7), 285 (pH 2), 275 (pH 11); $^1H$ NMR (500 MHz, DMSO-$d_6$) δ 1.23 (m, 1H), 1.94 (m, 1H), 2.01 (m, 1H), 3.42 (m, 2H), 3.80 (dd, J=4.5, 9.0 Hz, 1H), 4.01 (m, 1H), 4.54 (d, J=4.5 Hz, 1H), 4.59 (q, 1H), 4.65 (t, J=5.0 Hz, 1H), 4.72 (d, J=7 Hz, 1H), 5.69 (d, J=7.5 Hz, 1H), 6.96 (brs, 1H), 7.01 (brs, 1H) 7.60 (d, J=7.5 Hz, 1H); $^{13}C$ NMR (125 MHz, $CDCl_3$) δ 165.7, 156.6, 143.8, 93.8, 73.8, 72.1, 63.4, 61.7, 45.4, 29.0; Anal. Calcd for $C_{10}H_{15}N_3O_4$: C, 49.77; H, 6.27; N, 17.42. Found: C 49.67; H 6.31; N 17.43.

(1R,2S,3R,4R)-1-[2,3,Diacetoxy-4-(acetoxymethyl)-cyclopentan-1-yl]uracil (18). Compound 14 (5.7 g) was dissolved in $CF_3CO_2H/H_2O$ (2:1) (150 mL) and heated to 70° C. for 4 h. The solution was then concentrated under reduced pressure and coevaporated three times with methanol (3×200 mL). The residue containing 17 was dried under vacuum for overnight and it is used for next step directly. To a stirring solution of compound 17 (4.08, 16.85 mmol) in acetonitrile (100 mL), triethylamine (9.34 mL, 67.43 mmol), DMAP (41 mg, 0.33 mmol) fallowed by $Ac_2O$ (6.38 mL) were added at rt and stirred for 30 min. To mixture methanol (5 mL) was added and stirred for 10 min. The solvent was evaporated by vacuum to obtain white crude product. This was purified using silica gel column chromatography (EtOAc:Hexane=1:1) to give 18 (5.58 g, 90%) as a foam. $^1H$ NMR (500 MHz, $CDCl_3$) δ 1.73 (m, 1H), 2.04 (s, 3H), 2.10 (s, 6H), 2.39 (m, 1H), 2.52 (m, 1H), 2.51 (m, 2H), 4.79 (q, 1H), 5.24 (d, J=5 Hz, 1H), 5.43 (t, J=8 Hz, 1H), 5.77 (d, J=6 Hz, 1H), 7.20 (d, J=7.5 Hz, 1H), 9.35 (s, 1H); $^{13}C$ NMR (500 MHz, $CDCl_3$) δ 170.8, 170.1, 169.8, 163.0, 150.7, 141.7, 103.0, 73.1, 72.0, 64.2, 60.8, 40.0, 27.7, 20.8, 20.7, 20.6; HRMS-ESI (m/z): $(M+H)^+$ calcd for $C_{16}H_{20}N_2O_8$, 369.1299; found, 369.1298.

(1R,2S,3R,4R)-1-[2,3,Diacetoxy-4-(acetoxymethyl)-cyclopentan-1-yl]-5-fluorouracil (19) To a mixture of 18 (1.92 g, 5.21 mmol), selectfluor (2.03 g, 5.73 mmol) in acetonitrile (50 mL), AcOH (4 mL) was added at rt and stirred at 95° C. for 3 h. The mixture was diluted with ethyl acetate (200 mL), washed with $H_2O$ (100 mL) and saturated $NaHCO_3$ solution (2×100 mL). The organic layer was dried over $Na_2SO_4$ and concentrated under reduced pressure and dried over night with high vacuum. The crude residue was treated with $Et_3N$ (100 mL) and stirred at 95° C. for 3 h. The solvent was evaporated and purified using silica gel column chromatography (EtOAc:hexane=4:6) to give 19 (1.44 g, 72%) as a white foam. $^1H$ NMR (500 MHz, $CDCl_3$) δ 1.71 (m, 1H), 2.05 (s, 3H), 2.10 (s, 3H), 2.12 (s, 3H), 2.39 (m, 1H), 2.52 (m, 1H), 2.51 (m, 2H), 4.17 (dd, J=5.5, 12 Hz, 1H), 4.21 (dd, J=5.5, 12 Hz, 1H), 4.82 (q, 1H), 5.21 (t, J=6 Hz, 1H), 5.38 (m, 1H), 7.33 (d, J=6 Hz, 1H), 9.21 (s, 1H); $^{19}F$ NMR ($CDCl_3$, 500 MHz) δ-164; HRMS-ESI (m/z): $(M+H)^+$ calcd for $C_{16}H_{19}FN_2O_8$, 387.1204; found, 387.1208.

(1R,2S,3R,4R)-1-[2,3-Dihydroxy-4-(hydroxymethyl)-cyclopentan-1-yl]-5-fluorocytosine (20). A mixture of 19 (3.5 g, 9.06 mmol) and 4-dimethylamino-pyridine (2.21 g, 18.13 mmol) in anhydrous acetonitrile (100 mL), triethylamine (2.5 mL, 18.13 mmol) followed by 2,4,6-triisopropylbenzenesulfonyl chloride (5.49 g, 18.13 mmol) was added at rt under nitrogen. After being stirred for 12 h, $NH_4OH$ (30%, 150 mL) was added and stirred for 5 hours. The mix was concentrated under vacuum and the residue was purified using amine functionalized silica gel column chromatography (CH$_2$Cl$_2$: MeOH=5:1) fallowed by C$_{18}$ silica gel chromatography (water:methanol=8:2) to give 20 (1.77 g, 76%) as a foam. UV (H$_2$O) $\lambda_{max}$ 284 nm (pH 7), 293 nm (pH 2), 284 nm (pH 11); $^1$H NMR (500 MHz, DMSO-d$_6$) δ 1.21 (m, 1H), 1.92 (m, 1H), 2.01 (m, 1H), 3.42 (m, 2H), 3.72 (q, 1H), 3.99 (m, 1H), 4.54 (d, J=4.5 Hz, 1H), 4.59 (q, 1H), 4.65 (t, J=5.5 Hz, 1H), 4.76 (d, J=6.5 Hz, 1H), 7.36 (brs, 1H), 7.60 (brs, 1H) 7.96 (d, J=7.5 Hz, 1H); HRMS-ESI (m/z): (M+H)$^+$ calcd for C$_{17}$H$_{14}$FN$_3$O$_4$, 260.1047; found, 260.1044.

Biological Data

H5N1 Data (−)Carbodine (the D-nucleoside compound) and other enantiomers (the L-nucleoside compound as well as a racemic mixture) were tested in animals infected with Avian influenza A strain H5N1 virus at dilutions ranging from 1/100 to 1/1000 to determine inhibitory effect on the virus. The virus was that found in ducks, seagulls, a Hong Kong strain (HK/2003) ducks and a Vietnamese strain of H5N1 bird flu. In each of the four strains of H5N1 bird flu, (−)Carbodine, (+)Carbodine, a racemic mixture of the two enantiomers of Carbodine and ribivirin (an antiviral agent) were used. The results from the experiment appear in Table 1, attached in FIG. 1. The experiment shows that (−) carbodine exhibited good activity as an inhibitor of Avian Influenza A strain H5N1.

Figure 2:
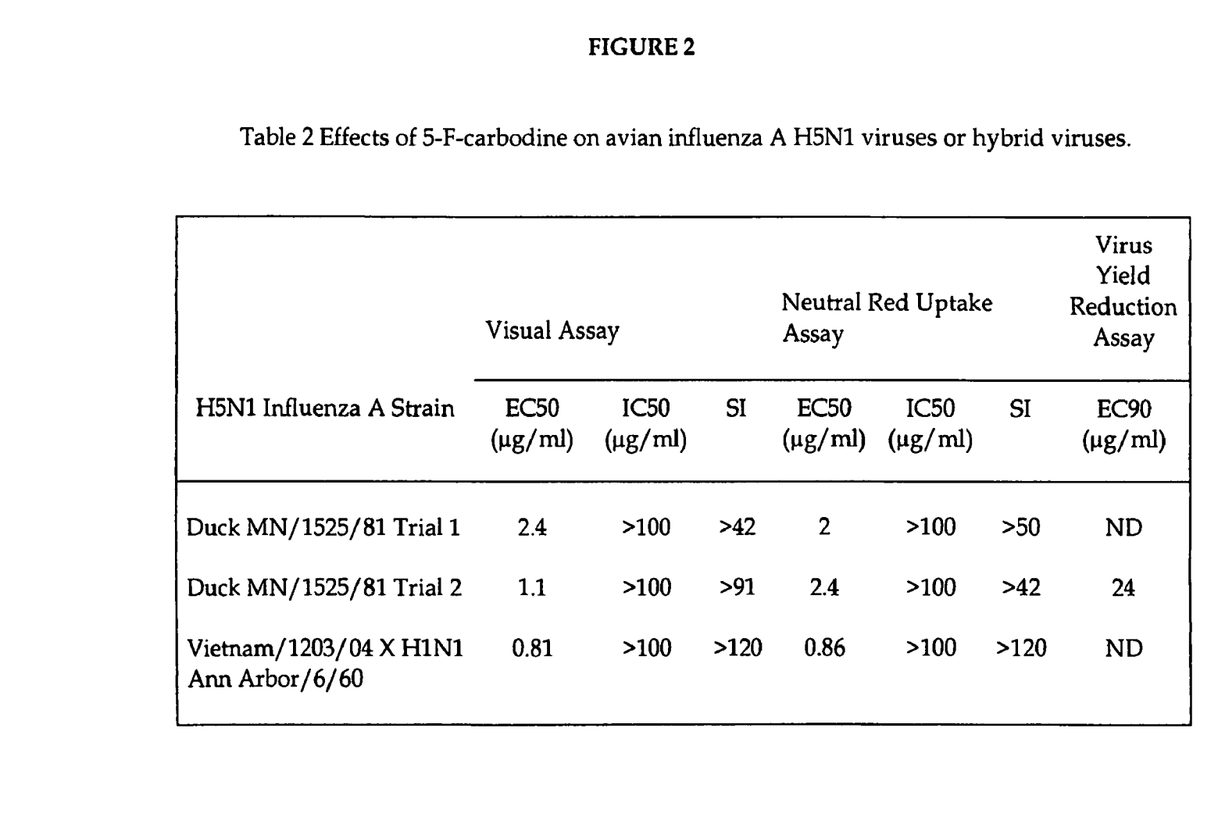
FIG. 2 shows the effects of 5-F-carbodine on avian influenza A H5N1 viruses or hybrid viruses.

In a separate experiment, the activity of 5-F carbodine was tested against avian influenza A H5N1 viruses or hybrid viruses. The results, which appear in attached FIG. 2, Table 2, evidence that 5-F carbodine is quite active in vitro against avian Influenza A H5N1 strain.

VEE Data

Figure 3:
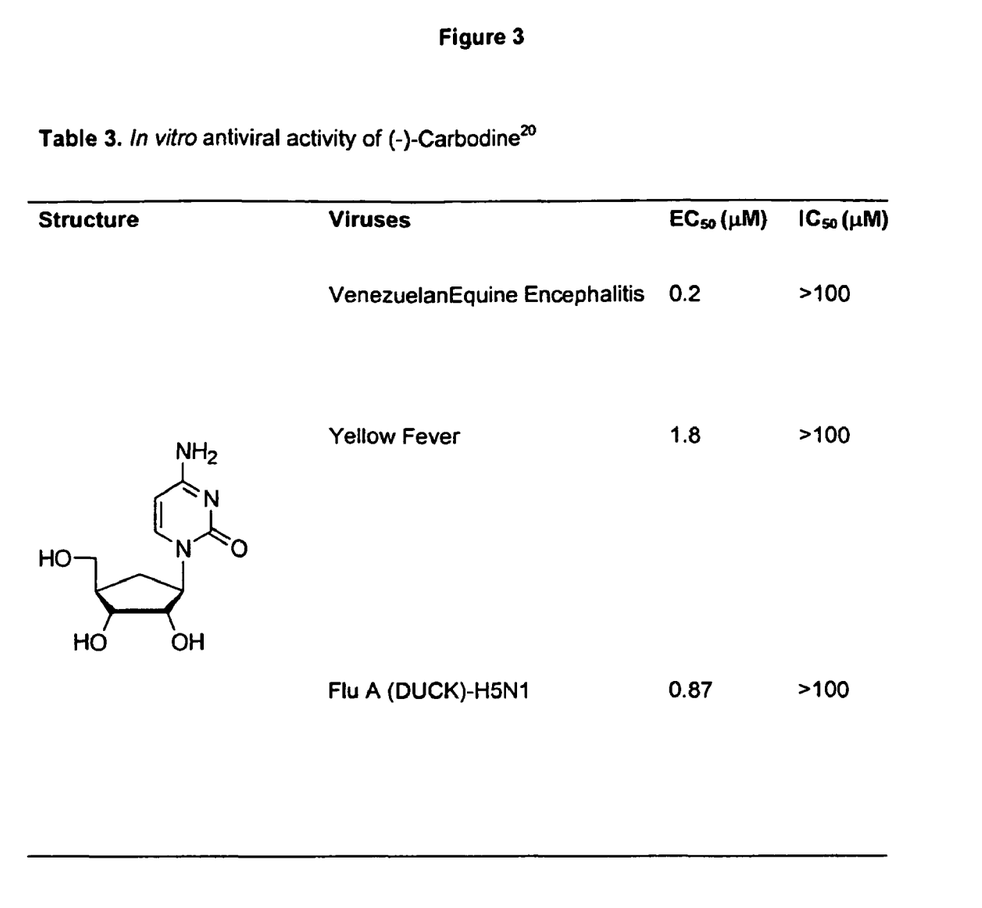
FIG. 3 shows In vitro antiviral activity of (−)-Carbodine against Venezuelan equine encephalitis virus, yellow fever virus and flu A (DUCK)-H5N1 virus (bird flu).

In Vitro (−) Carbodine was also tested in vitro against Venezuelan Equine Encephalitis (VEE) as well as yellow fever virus and H5N1. The results of that in vitro experiment appear in FIG. 3, Table 3. (−) carbodine evidenced good activity against VEE as well as H5N1 in the in vitro experiment.

In Vivo

Effect of Later Post-virus Administration of i.p. (−) Carbodine on Survival of Mice Infected with Venezuelan Equine Encephalitis Virus.

[(−)-carbodine] is an enatiomerically pure D-nucleoside that has been shown to be active against the vaccine strain (TC-83) of Venezuelan equine encephalitis virus (VEEV) in a C3H/HeN mouse model. An important consideration in the treatment of viral encephalatides is whether an effective compound will be useful in treatment after the establishment of virus infection in the brain has occurred. Virus is detectable in the brain 2 days post-virus installation (dpi), peaks at 4 dpi, and continues at high titers until death at around 9 dpi in this model of VEEV disease. A similar course of virus infection of the brain is seen in mouse models utilizing a molecular clone of the pathogenic Trinidad Donkey (TrD) VEEV strain (1, 2). The main objective of this experiment is to determine if treatment initiated at the time of viral entry into the brain or when virus titers peak in the brain is effective in reducing mortality and other disease parameters in mice challenged intranasally (i.n.) with VEEV.

In previous experiments, ampligen has been used as a positive control compound. Positive results were generally obtained, but occasionally ampligen failed to improve disease parameters. This was likely due to incomplete mixing and solubilization of stock before aliquoting resulting in an unequal distribution of RNA between tubes. Another objective of this study was to reduce the experiment-to-experiment variability by preparing homogenous stock aliquots in sterile tubes.

Materials and Methods

Animals: Female C3H/HeN mice obtained from Charles River Laboratories (Wilmington, Mass.) between 16 and 18 g were used. Animals were randomly assigned to cages and individually marked with eartags. Mice were fed standard mouse chow and tap water ad libitum.

Test article: The compound (−) Carbodine was dissolved initially in DMSO, after which the solution was diluted in sterile saline to a final DMSO concentration of 10% and stored at 4° C. until use. Ampligen was obtained as a viscous solution from Hemispherx Biopharma (Philadelphis, Pa.) and was used undiluted at 12 mg/kg/d. Ampligen was heated to 50° C. prior to use to ensure a homogenous mixture of compound.

Venezuelan equine encephalitis virus: The TC-83 vaccine strain of VEE was obtained from ATCC and used after passage in vero cells. A 10$^{-2}$ dilution (10$^{7.4}$ 50% cell culture infectious doses/ml) of the virus was prepared, and animals were inoculated i.n. with 0.05 ml of the diluted virus.

Experimental design: Mice were treated i.p. with (−) carbodine at a dose of 200 mg/kg/day starting 2 or 4 days post-intranasal virus installation (dpi). Placebo control mice were treated with 10% DMSO in saline on the same schedule as GYS-VI-16-23 treatment initiated −4 h prior to virus challenge. Mortality was checked daily for 21 days. Mice were weighed on the day of virus challenge and on 7 and 9 dpi. Ampligen was used as a positive control at 12 mg/treatment given −4 h and 2 dpi. A group of sham-infected mice treated bid, 2 to 9 dpi with 200 mg/kg/d of GYS-VI-16-23 was included as a toxicity control and weights were taken at 0, 7, and 9 dpi.

To reduce the variability of results obtained with ampligen treatment, ampligen stock solution was heated to 50° C. for 15 minutes prior to aliquoting to ensure a homogenous mixture of RNA. The ampligen solution was gently mixed after heating by inverting the stock tube several times, aliquoted to sterile tubes, and frozen at −20° C.

Statistical analysis: Survival data were analyzed using the Wilcoxon log-rank survival analysis (JMP™ software, The Statistical Discovery Software, SAS Institute, Inc). All other statistical analysis was done using one-way Students T-test.

Results and Discussion

Figure 4:
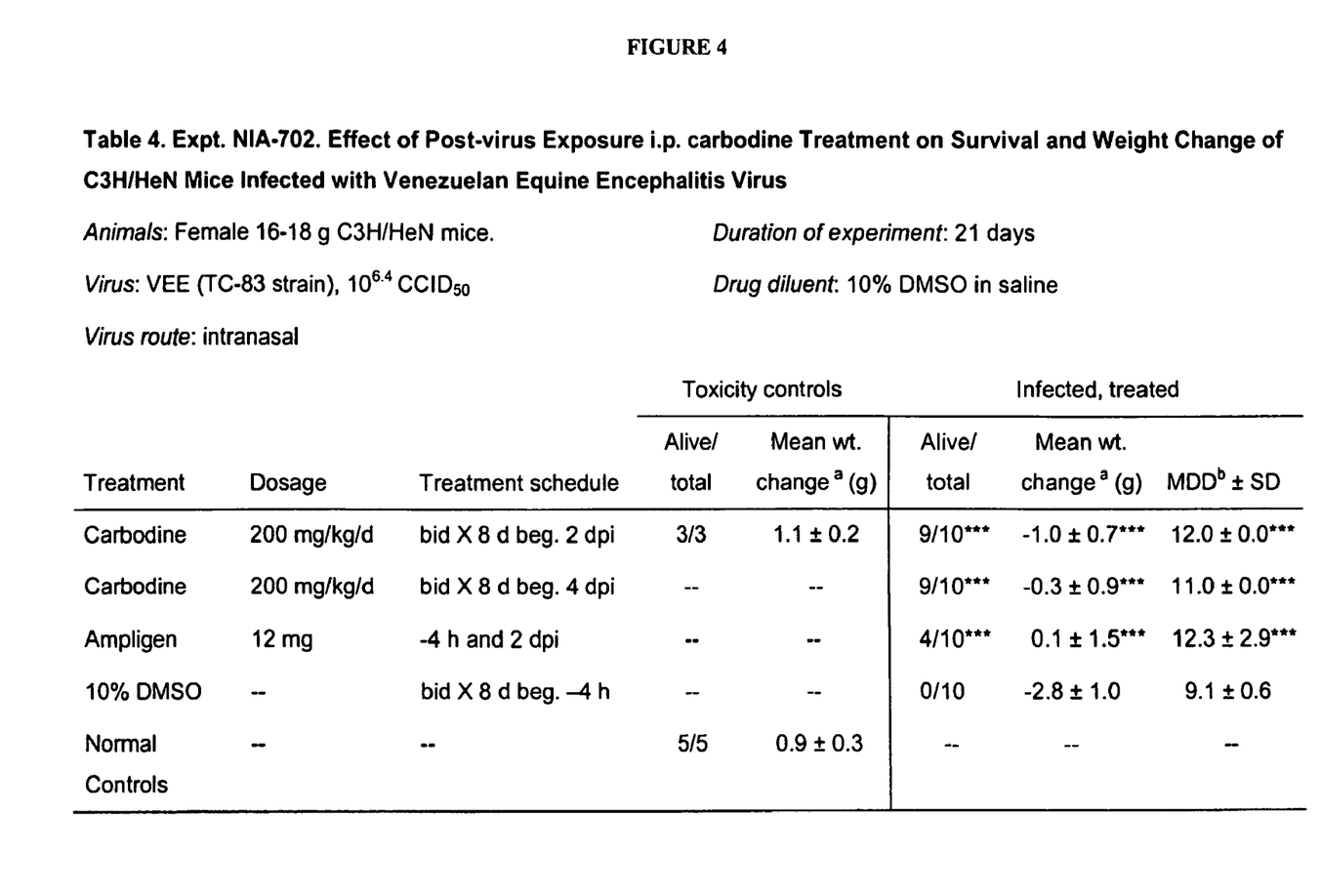
FIG. 4 shows the effect of post-virus exposure i.p. carbodine treatment on the survival and weight change of C3H/HeN mice infected with Venezuelan equine encephalitis virus.

Treatment i.p. with 200 mg/kg/d of GYS-VI-16-23, beginning 2 dpi and continuing with twice-daily treatments through 9 dpi, was efficacious in significantly improving survival, mean day to death, and weight gain (Table 4, FIG. 4). Later bid treatment with 200 mg/kg/d for 8 days beginning 4 dpi was also effective in significantly improving all disease signs measured. Virus peaks in the brain 4 dpi, so it is very remarkable that treatment initiated on the day of peak brain virus titer was effective in significantly improving disease. Virus titers remain constant in the brain after the peak at 4 dpi, and it would be interesting to see if treatment beginning later than 4 dpi is effective. Another study will be required to determine how long after virus challenge this compound will be efficacious.

It would also be interesting to see if treatment on or after 4 dpi would affect the brain titers in mice at later times during the course of infection. In a previous experiment (NIA-673, this report), titration of brain virus 4 dpi showed a 1-log reduction in virus titer. It would also be interesting to see if the titer continued to drop, if the reduction was sustained, or if virus rebounded. Carbodine is a known inhibitor of CTP synthase that converts UTP to CTP (3, 4) and results in a decrease of CTP pools, which affects replication of different viruses (5). If CTP pools are reduced, a steady decline in virus replication might be expected over the course of infection. Further studies will try to delineate the effect of treatment on the virus replication kinetics in the brain.

No toxicity was observed in this experiment with 200 mg/kg/d treatment beginning 2 or 4 days after virus infection as determined by weight change or mortality. In a previous experiment (NIA-673) weight loss was observed in sham infected mice treated with 200 mg/kg/d GYS-VI-16-23 given bid beginning 4 h prior to virus challenge. This could possibly be due to the timing of administration of the compound, with earlier treatment interacting in an unfavorable manner with virus infection parameters or host defense. This could also indicate a possible alternative mode of action of the compound, which may involve host parameters, making the timing of treatment administration an important consideration. It could also be simply an artifactual result due to the low number of mice used in toxicity control groups.

Ampligen treatment was effective as determined by a significant improvement in survival, mean day to death, and weight change. Further experiments using the aliquots prepared with the same stock used in this experiment determine if the preparation measures reduce the variability seen in past experiments.

Conclusions
- (−) Carboline 200 mg/kg/d, given i.p., bid for 8 days was effective in significantly improving survival, weight gain, and mean day to death when treatment was initiated 2 or 4 dpi.
- No toxicity was apparent with (−) Carboline treatment in sham-infected toxicity controls as determined by weight change and mortality.
- Ampligen was also effective in significantly improving survival, mean day to death and weight change when administered i.p. −4 h and 2 dpi at a dose of 12 mg/treatment.

REFERENCES

1. Schoneboom, B. A., K. M. Catlin, A. M. Marty, and F. B. Grieder. 2000. Inflammation is a component of neurodegeneration in response to Venezuelan equine encephalitis virus infection in mice. J Neuroimmunol. 109: 132-46.
2. Charles, P. C., J. Trgovcich, N. L. Davis, and R. E. Johnston. 2001. Immunopathogenesis and immune modulation of Venezuelan equine encephalitis virus-induced disease in the mouse. Virology. 284: 190-202.
3. De Clercq, E., J. Murase, and V. E. Marquez. 1991. Broad-spectrum antiviral and cytocidal activity of cyclopentenylcytosine, a carbocyclic nucleoside targeted at CTP synthetase. Biochem Pharmacol. 41: 1821-9.
4. Neyts, J., A. Meerbach, P. McKenna, and E. De Clercq. 1996. Use of the yellow fever virus vaccine strain 17D for the study of strategies for the treatment of yellow fever virus infections. Antiviral Res. 30: 125-32.
5. De Clercq, E., R. Bernaerts, Y. F. Shealy, and J. A. Montgomery. 1990. Broad-spectrum antiviral activity of carbodine, the carbocyclic analogue of cytidine. Biochem Pharmacol. 39: 319-25.

The invention claimed is:

1. A method of treating a Venezuelan equine encephalitis viral infection in a patient in need of therapy comprising administering to said patient an effective amount of a compound according to the chemical structure:

or a pharmaceutically acceptable salt thereof.

2. The method according to claim 1 wherein said compound is coadministered with an additional antiviral agent.

3. The composition according to claim 2 wherein said additional antiviral agent is repligen.

* * * * *